United States Patent
Okamoto et al.

(10) Patent No.: US 7,449,604 B2
(45) Date of Patent: Nov. 11, 2008

(54) PRODUCTION OF AROMATIC RING-CONTAINING AMINO COMPOUNDS AND CATALYSTS

(75) Inventors: Atsushi Okamoto, Niigata (JP); Toshio Watanabe, Niigata (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 64 days.

(21) Appl. No.: 11/517,360

(22) Filed: Sep. 8, 2006

(65) Prior Publication Data

US 2007/0060774 A1    Mar. 15, 2007

(30) Foreign Application Priority Data

Sep. 9, 2005  (JP) ............................. 2005-261558

(51) Int. Cl.
*C07C 209/48*    (2006.01)
(52) U.S. Cl. ........................ 564/385; 564/388; 526/915
(58) Field of Classification Search ........................ None
See application file for complete search history.

(56) References Cited

U.S. PATENT DOCUMENTS

| | | | |
|---|---|---|---|
| 3,923,891 A | 12/1975 | Greenfield et al. | |
| 4,482,741 A | 11/1984 | Kurek | |
| 5,569,802 A | 10/1996 | Luken et al. | |
| 6,066,589 A * | 5/2000 | Malentacchi et al. | 502/185 |
| 2002/0068843 A1 | 6/2002 | Dai et al. | |

FOREIGN PATENT DOCUMENTS

| | | |
|---|---|---|
| EP | 1 378 504 A2 | 1/2004 |
| EP | 1 394 146 A1 | 3/2004 |
| EP | 1 491 656 A1 | 12/2004 |
| GB | 814631 | 6/1959 |
| GB | 852972 | 11/1960 |
| GB | 962235 | 7/1964 |
| GB | 1149251 | 4/1969 |
| JP | 51-24494 | 2/1976 |
| JP | 53-020969 | 2/1978 |
| JP | 54-041804 | 4/1979 |
| JP | 56-063944 | 5/1981 |
| JP | 10-072377 | 3/1998 |
| JP | 10-101584 | 4/1998 |
| JP | 2002-205980 | 7/2002 |
| JP | 2002-226440 | 8/2002 |
| JP | 2004-269510 | 9/2004 |
| WO | WO 2005/026101 | 3/2005 |

OTHER PUBLICATIONS

European Search Report dated Jan. 23, 2007, for EP 06119525.1-2103.

* cited by examiner

*Primary Examiner*—Brian J Davis
(74) *Attorney, Agent, or Firm*—Antonelli, Terry, Stout & Kraus, LLP.

(57) ABSTRACT

An aromatic dinitrile compound is hydrogenated in an amide solvent in the presence of a solid catalyst and in the absence of ammonia to produce an aromatic ring-containing amino compound by reducing at least one cyano group to aminomethyl group. The solid catalyst is a supported palladium catalyst in which palladium is substantially present on the outer surface of carrier and in a surface layer within a depth of 200 μm from the outer surface. Using such a solid catalyst, the aromatic dinitrile compound is efficiently hydrogenated to the aromatic ring-containing amino compound under mild conditions.

15 Claims, 1 Drawing Sheet outer surface of carrier

PRODUCTION OF AROMATIC RING-CONTAINING AMINO COMPOUNDS AND CATALYSTS

BACKGROUND OF THE INVENTION

1. Field of the Invention

The present invention relates to a method of producing aromatic ring-containing amino compounds by hydrogenating an aromatic dinitrile compound in the presence of a solid catalyst and relates to the catalyst for use in such a production method.

2. Description of the Prior Art

A method of producing an aromatic ring-containing amino compound by a catalytic hydrogenation of an aromatic dinitrile compound in the presence of a solid catalyst to reduce the cyano group has been known. In most cases, the solvent for such a method is wholly or partly composed of liquid ammonia. As the solid catalyst, proposed are nickel and/or cobalt-containing catalysts (JP 53-20969B, UK Patent 1149251 and UK Patent 852972) and palladium-containing catalysts (JP 51-24494B, JP 2004-269510A, UK Patent 814631 and WO 2005/026101). It is taught that amine compounds are produced in a good reaction selectivity in the proposed methods because the unfavorable side reaction is prevented by the use of liquid ammonia solvents. However, the proposed methods involve serious drawbacks because the liquid ammonia solvent dissolves the catalytic metal component to destabilize the catalytic activity, a high-pressure apparatus is needed because of a high vapor pressure of liquid ammonia, and a process for vaporizing, recovering and recycling liquid ammonia is intricate to increase production costs.

As a method using no liquid ammonia, proposed is a hydrogenation using a sponge-form nickel and/or cobalt catalyst (Raney, trademark) in an organic solvent such as lower alcohols and ether compounds (JP 38-8719B and JP 54-41804A). The method of using the sponge-form catalysts involves drawbacks because the preparation of the sponge-form catalysts requires a leaching step using a chemical and a step of replacing the leaching aqueous solution with a reaction solvent, the catalyst is easily re-oxidized by oxygen, and the catalyst has a poor moldability. In the hydrogenation using the sponge-form catalyst, since a basic inorganic compound is also used to increase the reaction selectivity, an additional treatment for removing the basic inorganic compound is required after the reaction, to make the production system disadvantageous.

It is well known in the art that the catalytic hydrogenation of nitrile compounds can be performed generally under mild conditions (reaction temperature, pressure, etc.) in the presence of a noble metal catalyst rather than a catalyst containing a base metal such as nickel and cobalt because of a higher hydrogenating activity of the noble metal catalyst (Practical Catalytic Hydrogenation, Morris Freifelder (1971) John Wiley & Sons, Inc., Chapter 12 Nitriles p 240, and Studies in Surface Science and Catalysis,vol. 27, Catalytic Hydrogenation, L. Cerveny (1986) Elsevier, Chaper 4 Hygrogenation of Nitriles, p 105-144). Therefore, the hydrogenation in an organic solvent in the presence of a noble metal catalyst would provide an economically best production method, if such a hydrogenation can be effectively carried out. However, it has been known that the hydrogenation using a palladium catalyst without liquid ammonia produces, in addition to primary amines, by-products such as secondary amines and tertiary amines due to intermolecular condensation, even when a simple compound such as aliphatic mononitrile is used as the starting compound (UK Patent 962235, JP 2002-226440A, and Comparative Example B, Part I of U.S. Pat. No. 3,923,891). Therefore, it is difficult to avoid the by-production of high-boiling products in the hydrogenation of a compound having two or more cyano groups.

It has been also known that the hydrogenation of an aromatic nitrile compound using a palladium catalyst causes another side reaction in addition to the side reaction mentioned above, in which the aminomethyl group of the hydrogenated product is further subjected to hydrogenolysis to a methyl group (Comparative Example B, Part I of U.S. Pat. No. 3,923,891 and Examples 1 and 2 of U.S. Pat. No. 4,482, 741). For example, it is reported that the yield of 1,3-bis (aminomethyl)benzene in the hydrogenation of isophthalonitrile in 2-methoxyethanol using a palladium catalyst is as low as 60%, showing the by-production of large amounts of high-boiling products due to intermolecular condensation and methylbenzylamine due to hydrogenolysis (Examples 1 and 2 of U.S. Pat. No. 4,482,741).

Therefore, it is absolutely necessary to prevent the above side reactions for the efficient production of the aromatic ring-containing amino compound by the hydrogenation of one or two cyano groups of an aromatic dinitrile compound to aminomethyl group using a palladium catalyst in the absence of ammonia. To prevent the side reactions, it has been proposed to add an additive to the reaction system. For example, it has been reported that a mixture of cyanobenzylamine and bis(aminomethyl)benzene is obtained in high yields by the hydrogenation in methanol solvent added with tetraalkylammonium hydroxide (JP 2002-205980A). It has been also reported that xylylenediamine is produced in high yields by introducing carbon dioxide gas into the reaction system (JP 56-63944A). However, the proposed method are disadvantageous because the decomposition of tetraalkylammonium hydroxide or the precipitation of insoluble carbonates occurs after the hydrogenation, to make the process difficult to operate, and because an additional step or apparatus for supplying or removing the additive is required.

As noted above, the method of producing an aromatic ring-containing amino compound by the hydrogenation of an aromatic dinitrile compound using a supported palladium catalyst has been reported in many known documents. However, none of such documents describe or address the location of the supported palladium in the catalyst, particularly, the relationship between such a location and the reaction selectivity.

In addition, the catalytic hydrogenation of an aromatic nitrile compound using a palladium/ruthenium-containing catalyst is reported in many documents. For example, U.S. Pat. No. 4,070,399 discloses a hydrogenation of phthalonitrile using a palladium/ruthenium catalyst. However, in the proposed hydrogenation, the aromatic ring is also hydrogenated together with the cyano group to give bisaminomethylcyclohexane, thereby failing to teach the production method of an aromatic ring-containing amino compound.

It is also reported that a catalyst containing ruthenium and a group VIII element such as palladium which are supported on a carrier having macro pores with specific diameter size is usable for the hydrogenation of aromatic dinitriles (JP 10-72377A and JP 10-101584A). However, these documents provide nothing about the kinds of the hydrogenated products, the supporting region of the metal components, the effect achieved by the binary system of metal components, and the working examples.

SUMMARY OF THE INVENTION

An object of the present invention is to solve the above problems in the prior art and to provide a simple method of efficiently producing an aromatic ring-containing amino compound by the hydrogenation of an aromatic dinitrile compound in the presence of a solid catalyst under mild reaction conditions.

As a result of extensive research on the hydrogenation of an aromatic dinitrile compound in the presence of a solid catalyst, the inventors have found that the aromatic ring-containing amino compound is efficiently produced by the hydrogenation of the aromatic dinitrile compound in the presence of a supported palladium catalyst in which palladium is supported in the limited region of the carrier. The present invention is based on this finding.

Namely, the present invention relates to a method of producing an aromatic ring-containing amino compound, which includes a step of hydrogenating an aromatic dinitrile compound in an amide solvent in the presence of a solid catalyst and in the absence of ammonia, thereby reducing at least one cyano group to an aminomethyl group, the solid catalyst being a supported palladium catalyst in which most of palladium is present on an outer surface of a carrier and in a surface layer within a depth of 200 μm from the outer surface. The present invention is further relates to such a supported palladium catalyst.

DETAILED DESCRIPTION OF THE INVENTION

Figure 1:
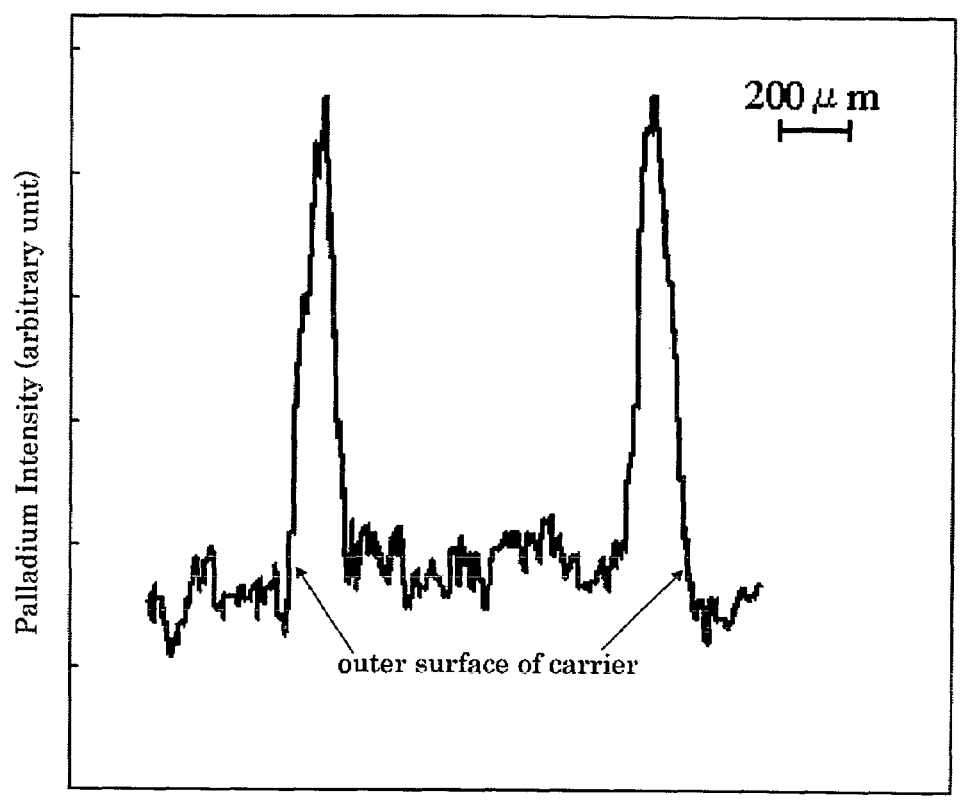
FIG. 1 is a chart showing the result of electron probe microanalysis on the alumina-supported palladium catalyst prepared in Example 3.

The aromatic dinitrile compound used in the present invention has two cyano groups which are directly bonded to the aromatic ring. Examples thereof include phthalonitrile, isophthalonitrile, terephthalonitrile, 1,5-dicyanonaphthalene, 1,8-dicyanonaphthalene, 2,6-dicyanonaphthalene, and 4,4'-dicyanobiphenyl. In addition to cyano group, the aromatic ring of the aromatic dinitrile compound may have another or other groups inert to the reaction, for example, alkyl groups such as methyl group and ethyl group, aryl group such as phenyl group, and alkoxy group such as methoxy group and ethoxy group. Of the aromatic dinitrile compounds, isophthalonitrile and terephthalonitrile are preferably used and isophthalonitrile is more preferably used because aromatic ring-containing amino compounds useful as intermediates or raw materials for the production of medicines, agricultural chemicals, polymer compounds, etc. can be obtained.

In the present invention, the compound obtained by reducing (hydrogenating) at least one cyano group of the aromatic dinitrile compound to aminomethyl group is referred to as "aromatic ring-containing amino compound." For example, 3-cyanobenzylamine and/or m-xylylenediamine can be produced from isophthalonitrile. Also, the compound obtained by reducing only one cyano group is referred to as "aromatic ring-containing monoamino compound," and the compound obtained by reducing both the cyano groups is referred to as "aromatic ring-containing diamino compound."

The solid catalyst used in the present invention is composed of a carrier supporting metal palladium. Examples of the carrier include activated carbon, alumina, silica, zirconia, titania, barium sulfate and zeolite, with alumina and silica being preferred because of their low costs and easiness of supporting operation. The BET specific surface area of the carrier is preferably from 10 to 600 m$^2$/g and more preferably from 30 to 300 m$^2$/g.

Any palladium compound can be used as the palladium source without particular limitation as far as it is soluble in water or organic solvents, and examples thereof include palladium chloride, tetrachloropalladates, tetraamminepalladium salts, palladium nitrate, and palladium acetate, with palladium chloride being most preferred because of its high solubility and practicability for industrial use. Palladium chloride is used after dissolved in an aqueous solution of sodium chloride, diluted hydrochloric acid, ammonia water, etc.

In the catalyst of the present invention, the metal palladium is unevenly supported on the outer surface of carrier and in the region close to the outer surface, to form an eggshell profile. Namely, basically most of the supported palladium is preferentially located on the carrier surface and in the surface layer ranging from the outer surface of the carrier to a depth of 200 μm. The region of the carrier in which most of palladium is preferentially supported may be referred to as "palladium-supporting layer." In the catalyst of the present invention, preferably 99% or more, more preferably 99.9% or more (each inclusive of 100%) of the total palladium is located on the outer surface of carrier and in the surface layer ranging from the outer surface to a depth of 200 μm. Still more preferably, most of the supported palladium (from 99 to 100%, preferably from 99.9 to 100% of the total palladium) is located on the outer surface of carrier and in the surface layer ranging from the outer surface to a depth of 150 μm. The amount of supported palladium is preferably from 0.05 to 10 wt % and more preferably from 0.2 to 5 wt % based on the whole weight of the catalyst.

According to the studies made by the inventors, it was found that the conversion of the aromatic dinitrile compound was very low when a standard catalyst where palladium is distributed to the core region of carrier is used, as compared with using the eggshell catalyst. This is presumably due to the failure of palladium supported in the core region to exhibit its catalytic activity because of the insufficient dispersion of the aromatic dinitrile compound dissolved in the reaction solvent into the core region. Therefore, it is preferred to support palladium on the outer surface and in the surface layer in view of effectively utilizing the catalytic activity of palladium.

As a result of extensive studies on the relationship between the thickness of the palladium-supporting layer and the catalytic function, it was found that the amount of by-products varied depending on the thickness whereas the conversion of the aromatic dinitrile compound was nearly the same until the thickness reached about 530 μm. Namely, the amount of by-products such as high-boiling products resulted from the condensation of the aromatic dinitrile compounds or the hydrogenated products and the decomposed products resulted from the subsequent hydrogenolysis of the produced aromatic ring-containing amino compound tends to increase as the distribution of palladium spreads into the inner region of the carrier, i.e., as the thickness of the palladium-supporting layer increases.

Although not elucidate in detail, this phenomenon is presumably due to a high polarity of the produced aromatic ring-containing diamino compound as compared with the starting aromatic dinitrile compound. With its higher polarity, the produced aromatic ring-containing diamino compound is strongly adsorbed onto the carrier or the palladium metal and held inside the carrier for long, and held more longer if the distribution of palladium spreads deeper into the inside of the carrier. Therefore, the produced aromatic ring-containing diamino compound is liable to undergo the side reactions to high-boiling products and decomposed products due to hydrogenolysis. Thus, it has been found that palladium should be distributed preferentially on the carrier surface and in the surface layer close to the carrier surface in order to obtain the aimed products in high yields. To ensure such high yields, it is preferred to regulate the thickness of the palladium-supporting layer within the above range.

The supported eggshell palladium catalyst mentioned above is produced by a known method, for example, an impregnation method and a spray method described in Journal of the Chemical Society of Japan, 1991, 4, 261-268 and Atsumu Ozaki *Chemistry of Catalyst Preparation,* Kodansha Ltd.: Tokyo, 1980; p 56. In the impregnation method, the carrier is impregnated with a solution prepared, for example, by dissolving a palladium compound in an aqueous solution of sodium chloride. The concentration of palladium in the impregnation solution is preferably from 0.05 to 4% by weight, and the pH thereof is preferably from 1 to 11. The impregnation temperature is preferably from 10 to 90° C., and the impregnation time is preferably from 5 min to 100 h. The conditions for impregnation are suitably selected from the respective conditions mentioned above and optimized by one of ordinary skill in the art so that most of the palladium compound is preferentially distributed on the outer surface of carrier and in the surface layer within 200 μm from the outer surface. In the spray method, a solution prepared, for example, by dissolving a palladium compound in an aqueous solution of sodium chloride is sprayed onto the catalyst carrier and dried, to support the palladium compound on the outer surface and in the surface layer.

After supported on the carrier in the eggshell profile, the palladium compound is reduced to palladium metal before use. The reducing agent, reducing method and reducing conditions can be selected from those known in the art. For example, the carrier supporting the palladium compound is brought into contact with a solution containing a reducing agent such as formaldehyde-sodium hydroxide, sodium formate, hydrazine, sodium hypophosphite, and sodium borohydride, or a reducing gas such as hydrogen gas, carbon monoxide and methanol vapor.

The supported palladium catalyst of the invention may further support ruthenium and/or magnesium. Namely, the catalyst of the present invention includes a supported palladium catalyst, a supported palladium/ruthenium catalyst, a supported palladium/magnesium catalyst, and a supported palladium/ruthenium/magnesium catalyst. In the hydrogenation using such a catalyst, the aromatic ring-containing diamino compound is dominantly produced over the aromatic ring-containing monoamino compound. This effect of additional ruthenium and/or magnesium is not so noticeable immediately after the initiation of hydrogenation, but surprisingly, becomes quite remarkable after several hours to ten hours or so. The initial catalytic activity of the supported palladium catalyst to hydrogenate the aromatic ring-containing monoamino compound to the aromatic ring-containing diamino compound is liable to be deactivated. It is presumed that the deactivation of this ability is prevented by the additional ruthenium and/or magnesium, to promote the hydrogenation to the aromatic ring-containing diamino compound.

The location of the supported ruthenium in the carrier is not specifically limited as far as the effect of the present invention is not adversely affected. Although ruthenium may be distributed toward the center of the carrier, it is preferred that, as in the case of palladium, ruthenium is preferentially located on the carrier surface and in the surface layer ranging from the outer surface of the carrier to a depth of 200 μm. Similarly, the location of the supported magnesium in the carrier is not specifically limited, and magnesium may be distributed toward the center of the carrier beyond the above surface layer.

The amount of the supported ruthenium is preferably from 1 to 50 mol % and more preferably from 5 to 20 mol %, each based on the molar amount of the supported palladium, in view of maximizing the yield of the aromatic ring-containing diamino compound.

Any ruthenium compound can be used as the ruthenium source without particular limitation as far as it is soluble in water or organic solvents, and examples thereof include ruthenium nitrate, ruthenium trichloride, nitrosylruthenium trichloride, hexachlororuthenate, ruthenium acetylacetonate, and ruthenium carbonyl.

The order of supporting is also not critical, and ruthenium is supported simultaneously with palladium, supported in advance to supporting palladium, or supported after supporting palladium.

The ruthenium compound supported on the carrier is also reduced to metal ruthenium before use. Since the ruthenium compound is generally resistant to reduction as compared with the palladium compound, the reduction of the ruthenium compound requires severe conditions or reagents if it is solely reduced. If palladium coexists, the ruthenium compound is reduced under mild conditions to give a well-mixed state of palladium and ruthenium. Therefore, it is preferred to reduce the ruthenium compound simultaneously with the palladium compound, or to reduce the ruthenium compound after supporting palladium metal. For these reduction methods, nitrosylruthenium trichloride is particularly preferred.

The amount of the supported magnesium is preferably from 100 to 5000 mol % and more preferably from 100 to 2000 mol %, each based on the molar amount of the supported palladium, in view of maximizing the yield of the aromatic ring-containing diamino compound. Any magnesium compound can be used as the magnesium source without particular limitation as far as it is soluble in water or organic solvents, and examples thereof include magnesium nitrate, magnesium acetate and magnesium acetylacetonate. The order of supporting is also not critical, and magnesium is supported simultaneously with palladium, supported in advance to supporting palladium, or supported after supporting palladium. The magnesium compound supported on the carrier is converted into magnesium oxide by pyrolysis, calcination, etc. before use.

To finely deposit the palladium compound on the carrier, the basicity of the carrier is important. Since magnesium oxide acts as the basic sites on the carrier, it is preferred to support magnesium oxide on the carrier in advance of supporting the palladium compound. In an effective method, for example, the magnesium compound is supported on the carrier in advance, converted into magnesium oxide by calcination, and then, the palladium compound is supported on the carrier.

The shape of the carrier is not limited, and any of spherical carrier, cylindrical carrier, and particle carrier obtained by crushing the spherical or cylindrical carrier is usable. The average size of carrier particles is preferably from 0.5 to 5 mm.

In the present invention, the hydrogenation is performed in a known operation manner such a batchwise operation and a continuous operation. In view of production efficiency, the continuous operation in which the solvent containing the starting raw material (starting liquid) is continuously flowed is preferably employed. The solid catalyst is used in either a fluid bed manner or a fixed bed manner. Since palladium metal supported on the outer surface and surface layer of the catalyst is expensive, the fixed bed manner is preferable to the fluid bed manner in view of preventing the loss of palladium metal by abrasion.

In the continuous method, the hydrogenation can be performed under trickle flow conditions (trickle bed reaction system) or bubble flow conditions. The starting liquid is supplied to the reactor in the gravity direction (downflow) or in the opposite direction (upflow). The starting liquid and hydrogen gas are fed to the reactor in either a countercurrent manner or a parallel manner.

In the present invention, the term "in the absence of ammonia" means that the concentration of ammonia in the hydrogenation system is 1000 ppm or lower (inclusive of zero). By regulating the content of ammonia existing in the hydrogenation system within the above range, the disadvantages involved in the methods using liquid ammonia described above can be effectively avoided. In the present invention, a small amount of ammonia possibly present in the reaction system is attributed to the by-production during the hydrogenation or the recycled use of the reaction gas containing hydrogen. Therefore, the positive use of ammonia, for example, as a solvent, is not intended in the present invention.

Since the starting aromatic dinitrile compound has a high melting point and a low vapor pressure, the hydrogenation is generally carried out in a reaction solvent.

In the present invention, the amide solvent is preferably used as the reaction solvent because the aromatic rind-containing amino compound can be produced in high yields and the catalyst life can be prolonged in a continuous hydrogenation, as compared with using an ether solvent or an alcohol solvent. Particularly preferred examples thereof include N,N-dimethylformamide, N,N-dimethylacetamide, N-methyl-2-pyrrolidone and 1,3-dimethyl-2-imidazolidinone.

Although depending on the solubility, the concentration of the aromatic dinitrile compound in the starting liquid is preferably from 0.5 to 14% by weight. Within this range, a high batch yield or a high space time yield is achieved while preventing the condensation to reduce the amount of by-products.

In the batchwise hydrogenation, the reaction time is preferably from 0.5 to 24 h, and the charge ratio of aromatic dinitrile compound/catalyst (weight basis) is preferably from 0.01 to 1000%. In the continuous hydrogenation, the weight hourly space velocity of the aromatic dinitrile compound being fed is preferably from 0.01 to 0.2 $h^{-1}$.

The reaction temperature is preferably from 20 to 200° C. and more preferably from 50 to 120° C. Within this range, the hydrogenation proceeds at a sufficient rate and the side reactions are prevented to increase the yield of the aimed compound.

The reaction pressure (total pressure) is preferably from 1 to 20 MPa and more preferably from 2 to 15 MPa. The hydrogen gas fraction in total pressure is preferably over 80% and more preferably over 90%. Within this range, a sufficiently high hydrogenation rate and a high conversion of the aromatic dinitrile compound are achieved. The hydrogen gas to be used may be purified or not, and those of general grade used for industrial hydrogenation are fully sufficient for the purpose. A higher hydrogen gas purity in the hydrogenation atmosphere is preferable because the hydrogenation is promoted more highly with increasing hydrogen partial pressure. However, if needed, the hydrogen gas may be diluted with a gas inert to the hydrogenation such as helium, argon, nitrogen and methane.

When the hydrogenation is performed in the coexistence of a cyclic secondary amine, the yield of the aromatic ring-containing amino compound increases and the catalyst life is prolonged.

The cyclic secondary amine referred to herein is a compound having at least one saturated hetero-ring structure including at least one imino group (—NH—). The cyclic secondary amine having a 5- or 6-membered ring is particularly effective. Examples thereof include pyrrolidine, imidazolidine, piperidine, piperazine, indoline, and 1,2,3,4-tetrahydroquinoline. The ring-forming carbon atom of the cyclic secondary amine may have at least one substituent selected from alkyl group such as methyl group and ethyl group; aryl group such as phenyl group; and alkoxy group such as methoxy group and ethoxy group. These cyclic secondary amines may be use alone or in combination of two or more in any proportions. Of the above, pyrrolidine, piperidine and piperazine are preferably used because of their low costs and easy availability.

The cyclic secondary amine can be supplied to the reaction system in any manner as far as the aromatic dinitrile compound is hydrogenated in the coexistence of the cyclic secondary amine. The cyclic secondary amine, solely or in the form of solution in the starting liquid, is supplied to the reaction system stepwise or continuously.

It has been surprisingly found that the yield of the aromatic ring-containing amino compound is increased and the reduction of the yield with time is drastically prevented particularly in the continuous hydrogenation, when the aromatic dinitrile compound is hydrogenated in the coexistence of the cyclic secondary amine. This effect is characteristic to the cyclic secondary amine, and linear aliphatic secondary or tertiary amines and aromatic amines do not exhibit this effect.

The molar ratio of aromatic dinitrile compound/cyclic secondary amine in the reaction system is preferably from 0.1 to 5 and more preferably from 0.3 to 2. If less than 0.1, the effect is not noticeable. No additional effect is obtained even if exceeding 5, while making the aromatic dinitrile compound difficult to dissolve.

The production method of the present invention provides a mixture of the aromatic ring-containing monoamino compound and the aromatic ring-containing diamino compound. The product ratio of these compounds can be easily controlled by changing the initial charge of the aromatic dinitrile compound, the feeding rate of the starting liquid, the amount of catalyst used, reaction time, etc. By selecting the reaction conditions so as to minimize the production of the aromatic ring-containing monoamino compound, the aromatic ring-containing diamino compound is preferentially produced. It is difficult and not preferred, however, to completely prevent the production of the aromatic ring-containing monoamino compound because severe reaction conditions are required.

The reaction products are separated from the solvent and recovered by a known method such as distillation, extraction and crystallization. The aromatic ring-containing monoamino compound and the aromatic ring-containing diamino compound are separated from each other by a known method, for example, by the method described in JP 40-10133B and UK Patent 814631.

The solvent used in the hydrogenation can be recovered by a separating operation such as distillation and can be reused in the next run of hydrogenation. A small amount of by-products which are difficult to separate does not adversely affect even when remain in the solvent to be reused.

The present invention will be described in more detail with reference to the examples and comparative examples. However, it should be noted that the scope of the present invention is not limited by the following examples.

The thickness of the palladium-supporting layer in the catalyst was measured by the following method.

The catalyst particles were mounted in epoxy resin and then sectioned by grinding. The cross section was subjected to linear analysis by an electron probe microanalizer (EPMA). From the relationship between the depth from the outer surface of carrier and the amount of existing palladium, the region in which 99% or more of palladium was contained was determined. The thickness of the palladium-supporting layer was expressed by the thickness of such a region.

Apparatus: JSM-T330A and JSM-T300-FCS each manufactured by JEOL, Ltd.

Conditions for Analysis

Accelerating voltage: 20 kV

Beam current (probe current): 100 nA

Dispersive Crystal: Pd PET and Ru PET

The distributions of the supported palladium and ruthenium in the catalyst were determined by the following method.

The catalyst particles were mounted in epoxy resin and then sectioned by grinding. After coating with gold, the area to be analyzed was exposed by sputtering to remove the gold coating. Then, Time of Flight Secondary Ion Mass Spectrometry (TOF-SIMS) was carried out on the exposed area up to 300 μm depth at 25 μm intervals while shifting the analyzing field. The distributions of the supported palladium and ruthenium were evaluated by the ratios of the integrated signal intensities ($^{106}$Pd/$^{27}$Al and $^{102}$Ru/$^{27}$Al).

Apparatus: TFS-2100 TRIFT II manufactured by Ulvac-PHI, Inc.

Beam accelerating voltage: 15 kV

Analyzing field: 25 μm×100 μm

EXAMPLE 1

A commercially available 3-mmϕ cylindrical alumina carrier (BET specific surface area: 167 m$^2$/g, pore volume: 0.47 ml/g) was crushed to alumina particles having a size of 1.5 to 2.0 mm. The alumina particles were impregnated with a palladium chloride/sodium chloride aqueous solution (palladium: 0.14% by weight, sodium: 0.063% by weight) at 35° C. for 0.5 h, to allow palladium chloride to be adsorbed on the alumina particles. Then, a formaldehyde/sodium hydroxide aqueous solution was poured onto the alumina particles to quickly reduce palladium chloride to palladium metal. The alumina particles were washed with ion-exchanged water and dried to prepare an alumina-supported 0.5 wt % palladium catalyst. The thickness of the palladium-supporting layer was 80 μm.

A tubular reactor (inner diameter: 10 mm, length: 300 mm) was packed with 6 g of the catalyst. From the top of tubular reactor, a 3 wt % isophthalonitrile solution in N-methylpyrrolidone was continuously fed at a flow rate of 15.5 g/h while feeding hydrogen gas in parallel manner under 2.0 MPa, to perform the hydrogenation at 70° C. After 10 h from the initiation of reaction, the product solution sampled from the outlet of reactor was gas-chromatographically analyzed. The results are shown in Table 1.

EXAMPLE 2

In the same manner as in Example 1 except for changing the concentration of the palladium chloride/sodium chloride aqueous solution (palladium: 0.87% by weight, sodium: 0.38% by weight), an alumina-supported 0.5 wt % palladium catalyst was prepared. The thickness of the palladium-supporting layer was 180 μm. The results of the hydrogenation conducted under the same conditions as in Example 1 are shown in Table 1.

COMPARATIVE EXAMPLE 1

In the same manner as in Example 2 except for changing the concentration of the palladium chloride/sodium chloride aqueous solution (palladium: 0.87% by weight, sodium: 0.19% by weight) and additionally using ammonia water, an alumina-supported 0.5 wt % palladium catalyst was prepared. The thickness of the palladium-supporting layer was 530 μm. The results of the hydrogenation conducted under the same conditions as in Example 1 are shown in Table 1.

TABLE 1

|  | Examples | | Comparative |
| --- | --- | --- | --- |
|  | 1 | 2 | Example 1 |
| Conversion (%) | | | |
| IPN | 99.8 | 99.7 | 95.2 |
| Yield (%) | | | |
| CBA | 32.3 | 39.0 | 61.2 |
| MXDA | 64.9 | 54.3 | 19.1 |
| CBA + MXDA | 97.2 | 93.3 | 80.3 |
| MBA | 1.5 | 4.7 | 11.0 |
| High-boiling compounds | 0.6 | 1.5 | 3.5 |

IPN: isophthalonitrile
CBA: 3-cyanobenzylamine
MXDA: m-xylylenediamine
MBA: 3-methylbenzylamine
Yield: (Amount of each compound produced per unit time/Supplied amount of isophthalonitrile per unit time) × 100 (molar basis).

EXAMPLE 3

A commercially available spherical alumina carrier (BET specific surface area: 194 m$^2$/g, pore volume: 0.49 ml/g) was crushed to alumina particles having a size of 1.0 to 1.4 mm. The alumina particles were impregnated with a palladium chloride/sodium chloride aqueous solution (palladium: 0.87% by weight, sodium: 0.38% by weight) at 35° C. for 0.25 h, to allow palladium chloride to be adsorbed on the alumina particles. Then, a formaldehyde/sodium hydroxide aqueous solution was poured onto the alumina particles to quickly reduce palladium chloride to palladium metal. The alumina particles were washed with ion-exchanged water and dried to prepare an alumina-supported 0.4 wt % palladium catalyst. The thickness of the palladium-supporting layer was 180 μm.

A tubular reactor (inner diameter: 10 mm, length: 300 mm) was packed with 5 g of the catalyst. From the top of tubular reactor, a 6 wt % isophthalonitrile solution in N-methylpyrrolidone was continuously fed at a flow rate of 7.2 g/h while feeding hydrogen gas in parallel manner under 2.0 MPa, to perform the hydrogenation at 62° C. After 2 h from the initiation of reaction, the product solution was analyzed. The results are shown in Table 2.

EXAMPLE 4

The hydrogenation was performed in the same manner as in Example 3 except for changing the reaction temperature to 70° C. After 10 h from the initiation of reaction, the product solution was analyzed. The results are shown in Table 2.

EXAMPLE 5

The alumina particles obtained in Example 3 were impregnated with magnesium acetate. The alumina particles were then calcined in air at 400° C., to prepare an alumina carrier supporting 2.0 wt % magnesia. In the same manner as in Example 2, palladium was supported on the alumina carrier, to prepare an alumina-supported 0.4 wt % palladium/2.0 wt % magnesia catalyst. The thickness of the palladium-supporting layer was 180 μm.

Using the obtained catalyst, the hydrogenation was conducted in the same manner as in Example 4. The results are shown in Table 2.

TABLE 2

|  | Examples | | |
| --- | --- | --- | --- |
|  | 3 | 4 | 5 |
| Conversion (%) | | | |
| IPN | 100.0 | 100.0 | 100.0 |
| Yield (%) | | | |
| CBA | 9.0 | 25.6 | 20.6 |
| MXDA | 86.2 | 68.7 | 73.4 |
| CBA + MXDA | 95.2 | 94.3 | 94.0 |
| MBA | 3.1 | 4.2 | 5.2 |
| High-boiling compounds | 1.6 | 0.5 | 0.2 |

EXAMPLE 6

A tubular reactor (inner diameter: 10 mm, length: 300 mm) was packed with 5 g of the alumina-supported 0.4 wt % palladium catalyst prepared in Example 3. From the top of tubular reactor, a 6 wt % isophthalonitrile solution in N-methylpyrrolidone was continuously fed at a flow rate of 7.2 g/h while feeding hydrogen gas in parallel manner under 5.0 MPa, to perform the hydrogenation at 65° C.

After 10 h and 140 h from the initiation of reaction, the product solution was analyzed. The results are shown in Table 3.

COMPARATIVE EXAMPLE 2

In the same manner as in Example 6 except for using a 6 wt % isophthalonitrile solution in tetrahydrofuran in place of the 6 wt % isophthalonitrile solution in N-methylpyrrolidone, the hydrogenation was conducted. The results are shown in Table 3.

TABLE 3

|  | Example 6 | | Comparative Example 2 | |
| --- | --- | --- | --- | --- |
| Reaction time (h) | 10 | 140 | 10 | 140 |
| Conversion (%) | | | | |
| IPN | 100.0 | 100.0 | 100.0 | 100.0 |
| Yield (%) | | | | |
| CBA | 28.9 | 58.5 | 33.1 | 49.5 |
| MXDA | 69.3 | 37.3 | 61.4 | 34.7 |
| CBA + MXDA | 98.2 | 95.8 | 94.5 | 84.2 |
| MBA | 0.7 | 0.5 | 0.7 | 0.6 |
| High-boiling compounds | 0.4 | 2.9 | 2.7 | 12.3 |

EXAMPLE 7

A commercially available spherical alumina carrier (BET specific surface area: 194 m$^2$/g, pore volume: 0.49 ml/g) was crushed to alumina particles having a size of 1.0 to 1.4 mm. The alumina particles were immersed in a palladium chloride/nitrosylruthenium trichloride/sodium chloride aqueous solution (palladium: 0.15% by weight, ruthenium: 0.014% by weight, sodium: 0.063% by weight) at 35° C. for 0.25 h, to allow palladium chloride and nitrosylruthenium trichloride to be adsorbed on the alumina particles. Then, a formaldehyde/sodium hydroxide aqueous solution was poured onto the alumina particles to quickly reduce palladium chloride and nitrosylruthenium trichloride to palladium metal and ruthenium metal. The alumina particles were washed with ion-exchanged water and dried to prepare an alumina-supported 0.4 wt % palladium/0.04 wt % ruthenium catalyst. The thickness of the palladium-supporting layer was 85 μm.

A tubular reactor (inner diameter: 10 mm, length: 300 mm) was packed with 4.5 g of the catalyst. From the top of tubular reactor, a 9 wt % isophthalonitrile solution in N-methylpyrrolidone was continuously fed at a flow rate of 5.0 g/h while feeding hydrogen gas in parallel manner under 5.0 MPa, to perform the hydrogenation. The hydrogenation was continued for 280 h while gradually raising the temperature from 55° C. After 280 h, the temperature reached 59° C. After 15 h and 280 h from the initiation of reaction, the product solution was analyzed. The results are shown in Table 4.

EXAMPLE 8

The hydrogenation was conducted in the same manner as in Example 7 except for using the catalyst prepared in Example 7 and a 9 wt % isophthalonitrile/3.6 wt % piperidine solution in N-methylpyrrolidone. The results are shown in Table 4.

TABLE 4

|  | Example 7 | | Example 8 | |
| --- | --- | --- | --- | --- |
| Reaction time (h) | 15 | 280 | 15 | 280 |
| Conversion (%) | | | | |
| IPN | 100.0 | 100.0 | 100.0 | 100.0 |
| Yield (%) | | | | |
| CBA | 1.5 | 7.9 | 0.8 | 1.7 |
| MXDA | 96.1 | 80.2 | 97.7 | 92.0 |
| CBA + MXDA | 97.6 | 88.1 | 98.5 | 93.7 |
| MBA | 0.6 | 1.2 | 0.0 | 0.0 |
| High-boiling compounds | 0.0 | 8.9 | 0.0 | 4.8 |

EXAMPLE 9

In the same manner as in Example 7 except for changing the concentration of the palladium chloride/nitrosylruthenium trichloride/sodium chloride aqueous solution (palladium: 0.87% by weight, ruthenium: 0.087% by weight, sodium: 0.38% by weight), an alumina-supported 0.4 wt % palladium/0.04 wt % ruthenium catalyst was prepared. The thickness of the palladium-supporting layer was 180 μm.

Figure 2:
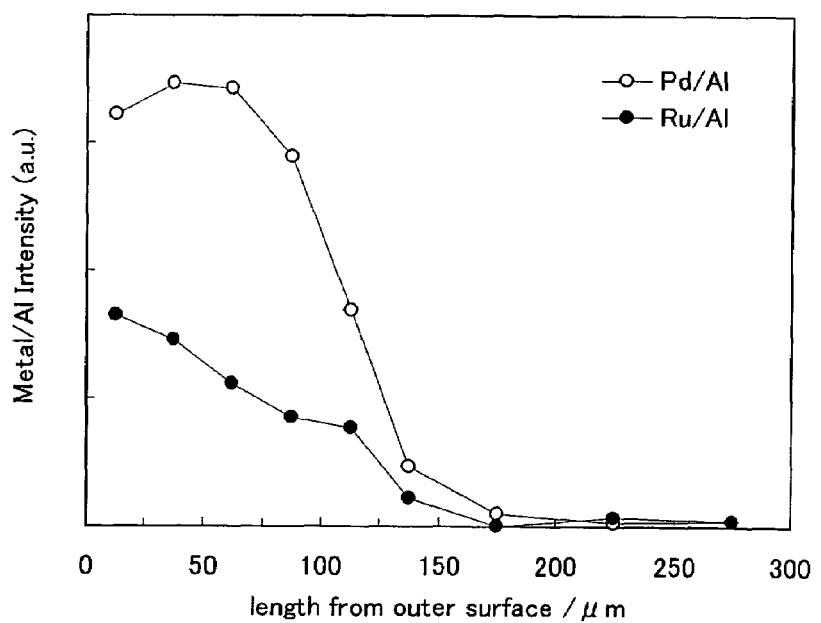
FIG. 2 is a chart showing the result of TOF-SIMS analysis on the alumina-supported palladium/ruthenium catalyst prepared in Example 9.

As a result of TOF-SIMS analysis on the catalyst thus prepared, it was found that the distributions of the supported palladium and ruthenium were in accord with each other as shown in FIG. 2.

What is claimed is:
1. A method of producing an aromatic ring-containing amino compound, which comprises a step of hydrogenating an aromatic dinitrile compound in an amide solvent in the presence of a solid catalyst and in the absence of ammonia, thereby reducing at least one cyano group to an aminomethyl group, the solid catalyst being a supported palladium catalyst in which 99% or more of palladium is present on an outer surface of a carrier and in a surface layer within a depth of 200 μm from the outer surface.

2. The method according to claim 1, wherein the hydrogenation is performed by a fixed bed continuous manner using the solid catalyst.

3. The method according to claim 1, wherein the solid catalyst further supports ruthenium and/or magnesium.

4. The method according to claim 1, wherein the aromatic dinitrile compound is isophthalonitrile.

5. The method according to claim 1, wherein the amide solvent is at least one compound selected from the group consisting of N,N-dimethylformamide, N,N-dimethylacetamide, N-methyl-2-pyrrolidone and 1,3-dimethyl-2-imidazolidinone.

6. The method according to claim 1, wherein the hydrogenation is performed in the presence of a cyclic secondary amine.

7. The method according to claim 6, wherein the cyclic secondary amine has at least one 5- or 6-membered, saturated hetero ring.

8. The method according to claim 7, wherein the cyclic secondary amine is at least one compound selected from the group consisting of pyrrolidine, imidazolidine, piperidine, piperazine, indoline, and 1,2,3,4-tetrahydroquinoline.

9. A solid catalyst comprising a carrier and (1) palladium and (2) at least one substance selected from the group consisting of ruthenium and magnesium, wherein the carrier supports both the palladium and said at least one substance, and 99% or more of the palladium is present on an outer surface of the carrier and in a surface layer within a depth of 200 μm from the outer surface.

10. The method according to claim 1, wherein 99.9% or more of the palladium is present on said outer surface and in a surface layer within a depth of 150 μm from the outer surface.

11. The method according to claim 1, wherein amount of supported palladium is from 0.05 to 10 wt.% based on the whole weight of the catalyst.

12. The solid catalyst according to claim 9, wherein 99.9% or more of the palladium is present on said outer surface and in a surface layer within a depth of 150 μm from the outer surface.

13. The solid catalyst according to claim 9, wherein amount of supported palladium is from 0.05 to 10 wt.% based on the whole weight of the catalyst.

14. The solid catalyst according to claim 9, wherein said at least one substance includes ruthenium, and amount of the ruthenium is 1-50 mol % based on the molar amount of the supported palladium.

15. The solid catalyst according to claim 9, wherein said at least one substance includes magnesium, and amount of the magnesium is from 100-5000 mol% based on the molar amount of the supported palladium.

* * * * *